United States Patent
Barrelle

(10) Patent No.: US 7,207,973 B2
(45) Date of Patent: *Apr. 24, 2007

(54) PASSIVE SAFETY SHIELD SYSTEM FOR INJECTION DEVICES

(75) Inventor: Laurent Barrelle, Saint Nizier du Moucherotte (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/288,699

(22) Filed: Nov. 6, 2002

(65) Prior Publication Data

US 2003/0212370 A1     Nov. 13, 2003

Related U.S. Application Data

(63) Continuation-in-part of application No. 10/143,414, filed on May 10, 2002, now Pat. No. 6,776,777.

(51) Int. Cl.
*A61M 5/32* (2006.01)
*A61M 5/00* (2006.01)

(52) U.S. Cl. ..................... 604/110; 604/198

(58) Field of Classification Search ............... 604/163, 604/110, 263, 192, 197, 198, 181, 187, 195, 604/264; 128/919
See application file for complete search history.

(56) References Cited

U.S. PATENT DOCUMENTS 6,776,777 B2 * 8/2004 Barrelle ............... 604/198
2002/0193746 A1 * 12/2002 Chevallier ............ 604/197

FOREIGN PATENT DOCUMENTS

EP      0966983   *  4/1999
FR      2794650   * 10/1999

* cited by examiner

*Primary Examiner*—Matthew DeSanto
(74) *Attorney, Agent, or Firm*—David M. Fortunato; Cohen, Pontani, Lieberman & Pavane

(57) ABSTRACT

A passive shield system for a syringe including a body, shield, spring and ring which provide an interlock of the shield in the retracted position prior to receipt of the syringe for bulk transportation and processing and wherein the user selects the timing of the release of the shield to its extended position following injection, but which assures shielding of the syringe needle following release of the syringe plunger.

11 Claims, 14 Drawing Sheets

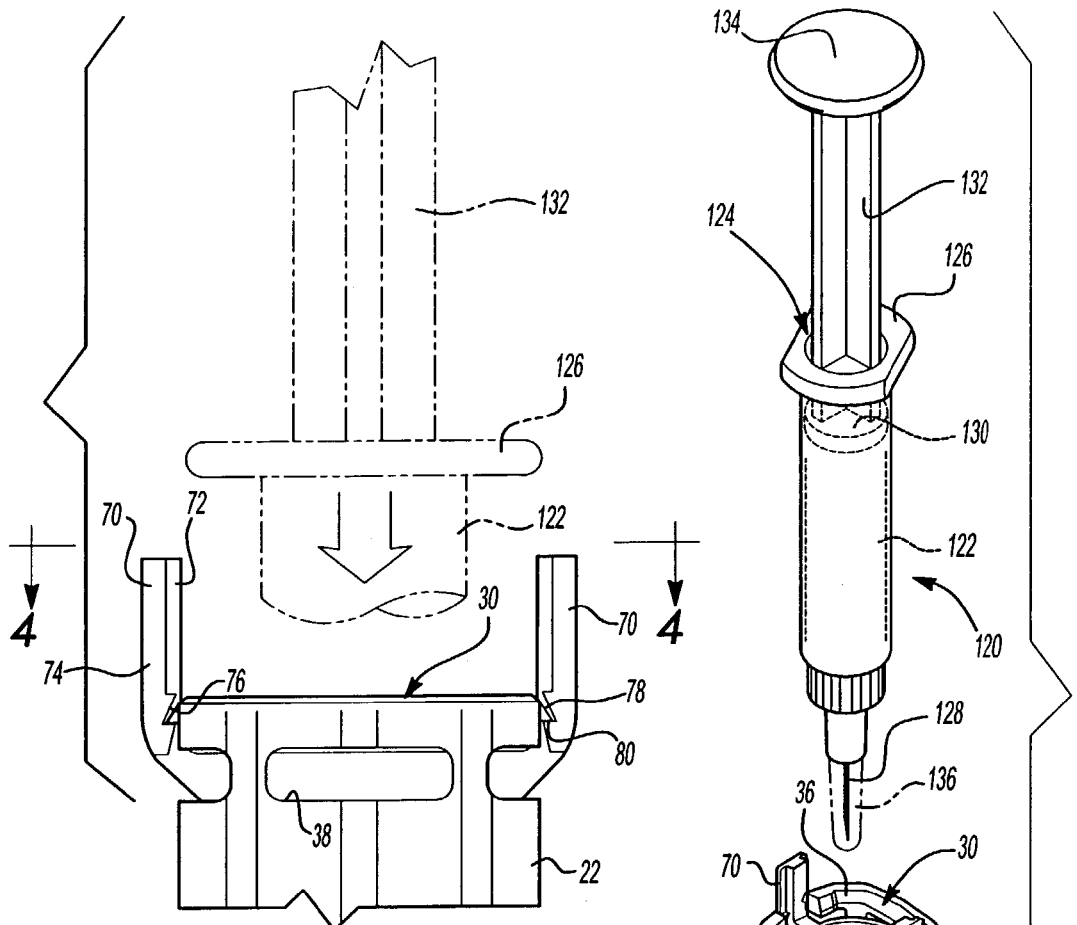
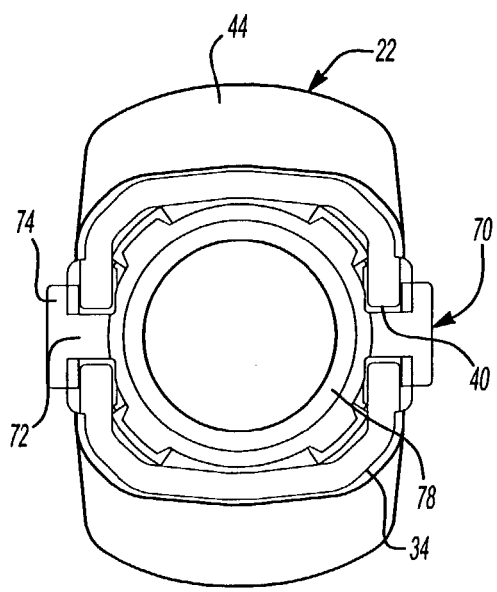
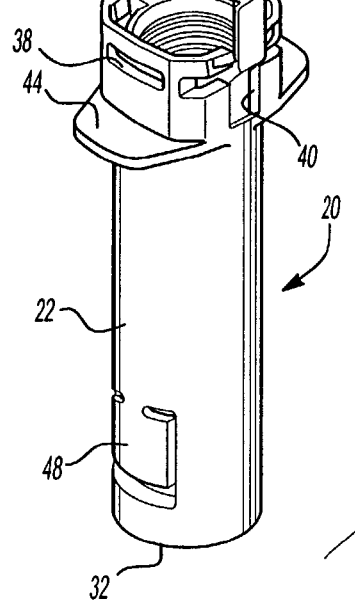
Fig-3
Fig-4
Fig-5

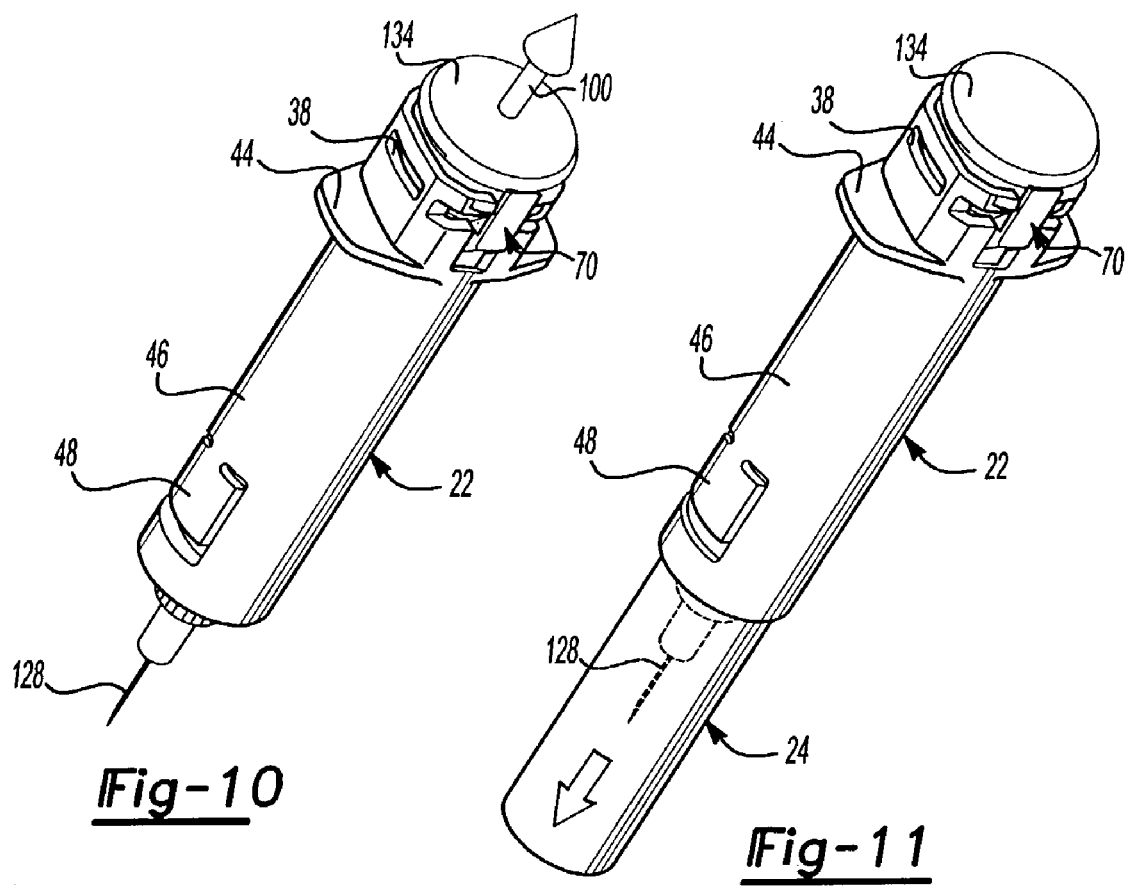

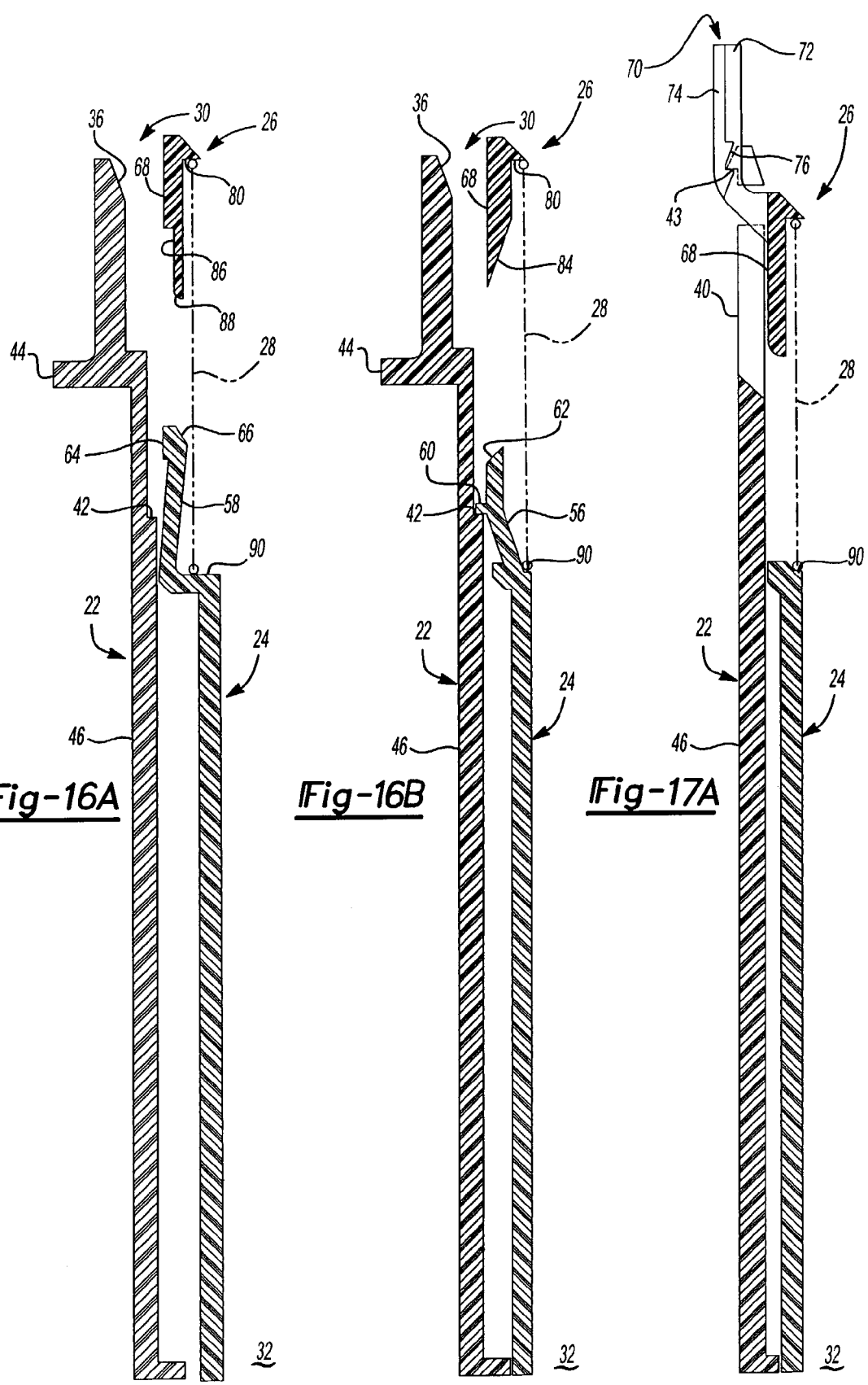

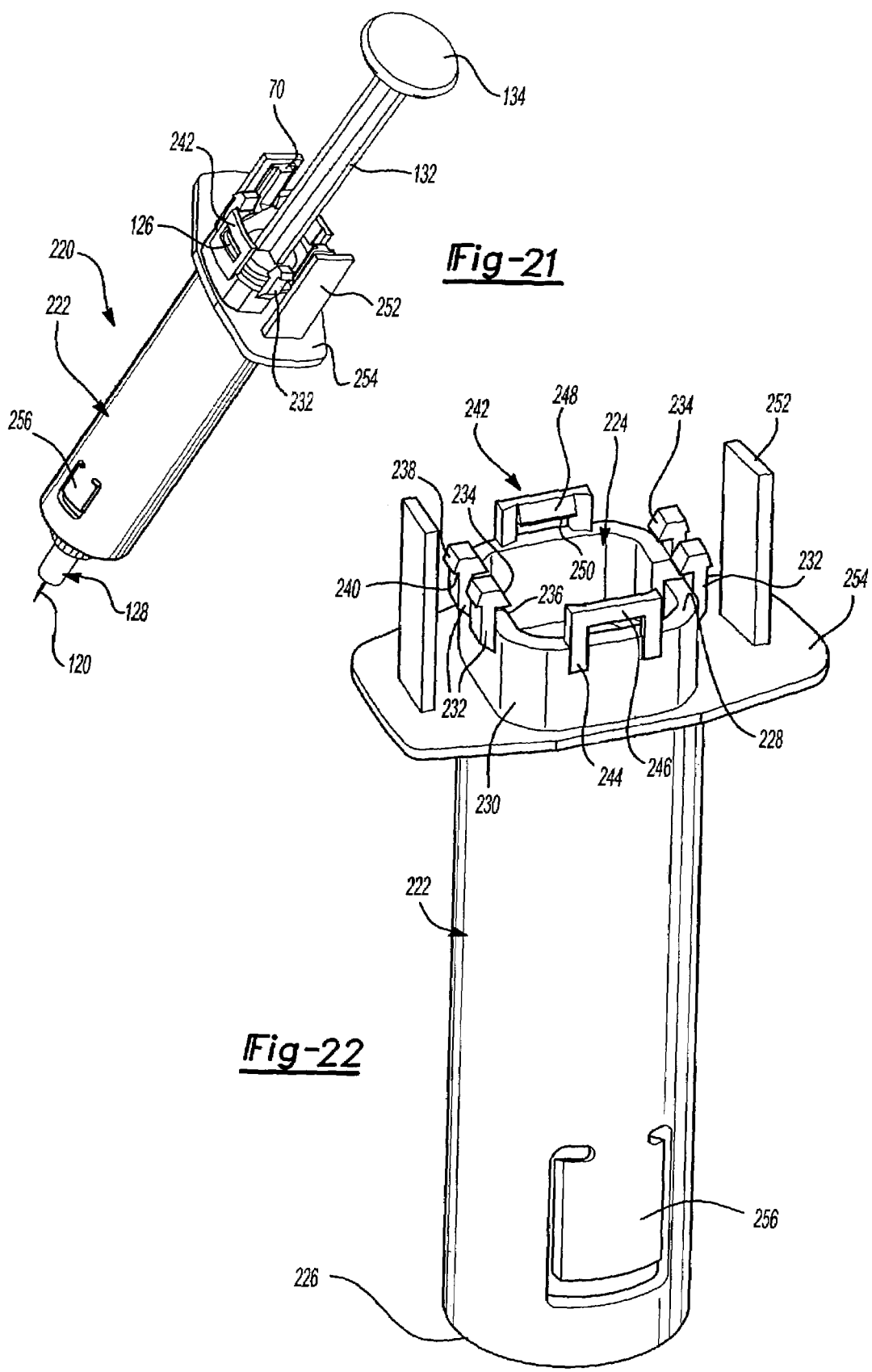

PASSIVE SAFETY SHIELD SYSTEM FOR INJECTION DEVICES

CROSS-REFERENCE TO RELATED APPLICATION

This application is a Continuation-In-Part of U.S. patent application Ser. No. 10/143,414, filed on May 10, 2002 now U.S. Pat. No. 6,776,777.

FIELD OF THE INVENTION

The present invention relates to a passive shield system for injection devices, including syringes, which prevents inadvertent or premature actuation of the shield during normal bulk transportation, handling and processing and permits the user, such as a healthcare worker or patient, to select the timing of the actuation of the shield while assuring shielding of the needle or cannula without additional manual manipulation.

BACKGROUND OF THE INVENTION

Injection devices including syringes are well known medical devices for administering medicaments, drugs and vaccines to patients. As used herein, the term "syringe" is intended to cover the various types of injection and medical delivery devices. Injection devices are also used for other well known purposes in the medical field, such as prefilled syringes, for example, which are generally considered as those syringes which are filled with a predetermined amount of medicament, drug or vaccine by a pharmaceutical manufacturer for distribution to the end user. Prefilled syringes are generally comprised of a tubular barrel, which contains the medicament, drug or vaccine and a plunger assembly slidably received in an open proximal end of the barrel. The distal end of the barrel typically includes a needle cannula affixed thereto or a connector for a hypodermic needle, such as a Luer fitting. The open proximal end of the syringe barrel generally includes an integral radial flange. The plunger assembly may be inserted by a pharmaceutical manufacturer following loading of the barrel with a suitable medicament, drug or vaccine. The plunger of a prefilled syringe generally includes a stopper, which is moveable in the syringe barrel, a plunger rod, which extends through the open proximal end of the barrel, and a thumb pad integrally formed on the end of the plunger rod. The syringe barrel is typically formed of glass, but may be formed of any suitable material including plastic and metal. The plunger allows the user to apply manual force (in a proximal to distal direction) to drive the stopper through the barrel thereby causing the medicament, drug or vaccine to be delivered through the needle cannula to the patient during an injection.

Health care providers are routinely exposed to the risk of an accidental needle stick, and consequently, the significant risk of exposure to disease resulting from a needle stick injury. To avoid accidental needle sticks, the prior art has proposed various types of safety shields for syringes. Such safety shields typically include a tubular shield which is located in a retracted position for injection and an extended position following injection enclosing at least the end point of the needle cannula of the syringe and preventing accidental needle sticks. The tubular shield of the syringe shield systems disclosed by the prior art are typically mounted on a body having a cavity for receipt of a syringe and the syringe is inserted into the body by the pharmaceutical company after filling the syringe with a suitable medicament, drug or vaccine. Alternatively, the shield may be mounted directly on the barrel of the syringe.

There are generally three types of prior art safety shield systems for syringes. The first type may be characterized as manual shield systems which require the user to manually move the shield from the retracted position, in which the needle is exposed for injection or aspiration in the case of reconstitution or vein test, to the extended position, in which the needle is enclosed by the shield. Such manual shield systems typically include some means to prevent the shield from being inadvertently moved to the extended position and prevent the shield from retracting following shielding of the syringe needle cannula, such as detents, interlocking ribs, threads, spiral grooves and the like. The principal disadvantages of manual syringe shield systems are that there is no positive assurance that the user will properly shield the needle cannula following use or that the shield is properly locked in the shielded position. In addition, some designs can allow inadvertent activation of the shield.

A second type of shield systems for syringes may be characterized as active shield systems. Active shield systems will typically include an energizer, such as a spring, which biases the shield toward the extended position. Generally, the shield is initially retained in the retracted position by ribs, detents or the like and actuated by some action by the user. The principal advantage of active syringe shield systems is that, upon activation by the user, the shield will be caused to move to enclose the needle cannula and lock the shield. Such active shield systems are generally activated by a button, movement of a component following injection or other release mechanism. That is, the user can generally activate the shield following injection to avoid contact of the shield with the patient's skin prior to disposal. The principal problem with active shield systems for syringes is that again there is generally no positive assurance that the end user will properly shield the needle cannula of the syringe.

The third type of shield systems may be characterized as passive shield systems. Passive shield systems also include an energizer, such as a spring, biasing the shield toward the extended position as described above in regard to the active shield systems. However, the shield system is activated automatically, generally upon completion of the injection. A disadvantage of the prior art passive shield systems is that the shield may be inadvertently or prematurely activated prior to use or completion of the delivery of the fluid in the syringe. That is, the shield can be activated while the needle cannula remains in the patient or the shield may be prematurely activated, particularly during normal manufacturing and assembly procedures and shipping. Shield systems are generally manufactured and assembled by the manufacturer of the shield system. The shield systems are then transported in bulk to a pharmaceutical company and must be handled using automatic feeding equipment, including feed bowls, etc., possibly resulting in inadvertent or premature activation of the shield.

The prior art also includes passive safety shield systems for syringes, wherein the shield system is actuated upon release of the plunger rod resulting in retraction of the syringe into the shield. However, in such shield systems, the syringe is withdrawn into the shield as the plunger rod is released, requiring the user to maintain the plunger against the force of the spring and requiring complete release of the plunger to shield the needle cannula of the syringe. In addition, the shield may contact the patient's skin.

There is thus a need for a shield system for syringes that overcomes the above-described shortcomings of the prior art.

SUMMARY OF THE INVENTION

The safety shield system of the present invention is passive, but avoids the above-described problems associated with the prior art passive shield systems. The shield system of the present invention may be utilized with prefilled syringes of the type described above, but may also be used with other types of injection devices. Premature or inadvertent actuation of the shield system is minimized by an interlock system which allows packing, transportation in bulk and handling using high speed feeding systems. Further, the shield is automatically caused to move to enclose the needle cannula by release of the plunger, thereby giving the user the option of releasing the needle cover only after complete delivery of the fluid in the syringe and removal of the needle cannula from the patient, while assuring shielding of the syringe needle cannula prior to disposal.

The passive shield system of the present invention includes four components: a body having an open proximal end for receipt of a syringe; a shield telescopically supported by the body and movable from a retracted position, in which the syringe needle cannula is exposed, to an extended position in which the needle cannula is enclosed; a spring biasing the shield toward the extended position; and an annular member which interlocks with the body to prevent premature actuation of the shield and which automatically actuates the shield upon release of the plunger. The shield is telescopically received within the body and moveable axially to shield the needle cannula of the syringe as described. The spring and the annular member are received in the open proximal end of the body such that the spring is positioned between the annular member and the shield. Prior to receipt of the syringe, the annular member serves as a locking member preventing premature actuation of the shield. The annular member includes a leg which forms a mechanical interlock with the body. In the disclosed embodiment, the annular member includes two opposed axially extending legs which, in the preferred embodiment, extend proximally, preferably beyond the open end of the body, for actuation of the shield as described below. The legs include opposed V-shaped locking surfaces which form a mechanical interlock with an opposed surface of the body adjacent the open proximal end preventing inadvertent or premature actuation of the shield during bulk shipping and processing as described above. In one disclosed embodiment, the projecting legs of the annular member are partially enclosed or surrounded by walls which minimize inadvertent release of the shield by the user. Upon loading of a syringe in the open proximal open end of the shield system, the syringe flange engages the proximal end of the annular member, driving the annular member distally and the legs of the annular member releasing the interlock between the annular member and the body for actuation of the shield as now described.

In the preferred embodiment of the shield system of the present invention, the tubular shield includes at least two fingers which extend axially from the proximal end of the shield, each having a radial portion which is received on an opposed radial support surface or ledge of the generally tubular body and releasably supports the shield on the body. The radial portions on the fingers are operatively spaced relatively axially, such that the fingers function independently during actuation of the shield as described below. However, the radial support surfaces or ledges on the body may alternatively be spaced axially and the radial portions of the fingers are then spaced axially only if required. One of the fingers is angled or bowed toward the radial support surface of the body, such that the angled or bowed finger is initially supported on the body prior to actuation of the shield. In a preferred embodiment, the shield includes four fingers, wherein two opposed pairs of fingers are angled or bowed toward the radial support surfaces of the body (referred to herein as the first pair of fingers) and the other pair of fingers extend generally axially or are bowed away from the body (referred to herein as the second pair of fingers), providing balanced support for the shield. When the tubular shield or needle cover is telescopically received within the body, as described above, the first pair of fingers are bowed or angled outwardly and the radial portions are spaced distally from the radial portions of the fingers which extend generally axially or are angled inwardly. The first pair of fingers therefore initially retains the shield in a first retracted position and the second pair of fingers retain the shield in a second retracted position.

Upon receipt of the syringe in the open proximal end of the shield system, the interlock between the body and the annular member is released and the annular member is free to move axially in the body against the force of the spring. The annular member includes a first camming surface or surfaces locked opposite the first pair of fingers and sized and shaped for interaction thereof. The annular member also includes a second camming surface or surfaces located opposite the second pair of fingers and sized and shaped for interaction thereof.

The shield is thus actuated in stages, as follows. First, as the injection is made, the thumb pad of the plunger assembly of the syringe engages the proximally extending legs of the annular member, driving the annular member distally in the body. The first camming surfaces of the annular member opposite the first pair of fingers then releases the first pair of fingers while the second camming surfaces of the annular member opposite the second pair of fingers simultaneously bias the second pair of fingers radially outwardly in releasable engagement with the opposed radial surfaces or ledges of the body, thereby releasably retaining the shield in a second retracted position. In a preferred embodiment, the second retracted position is close to or adjacent the first retracted position of the shield. Then, upon completion of the injection and release of the plunger by the user, the spring biases the annular member proximally, releasing the second pair of fingers from engagement with the radial surfaces or ledges of the body, and the shield is then driven distally to enclose the needle cannula as described. In a preferred embodiment, the body further includes opposed detents adjacent the distal end of the body which receive a radial portion or annular rib of the shield adjacent its proximal end which prevents retraction of the shield following actuation and movement of the shield from the extended position to the retracted position. The shield system of the present invention is thus passive in the sense that an additional action by the user is not required to activate the shield. That is, the shield is automatically activated upon release of the plunger. However, the user can also select the timing of the actuation of the shield, for example, by releasing the plunger after removal of the needle cannula from the patient, thereby eliminating engagement of the needle shield against the skin of the patient. Further, upon release of the syringe plunger by the user, the spring drives the shield from its second retracted position to its extended position, enclosing the syringe needle cannula, rather than retracting the syringe into the shield as disclosed in the prior art. Another advantage of the shield system of the present invention is that it may be used with conventional syringes without requiring special plungers, thumb pads, etc. A further advantage is that the shield system of the present invention may be designed for different sizes of syringes.

As set forth above, the syringe is received in the open proximal end of the shield system. In one embodiment, the syringe is retained in the body adjacent the open proximal end of the body by a cage which receives the flange of the syringe. In one disclosed embodiment, the cage includes inwardly inclined camming surfaces which are engaged by the flange of the syringe as the syringe is placed in the body. The cage also includes lateral openings within which the syringe flange rests when the syringe is placed in the body. Finally, the proximal end of the body includes axial slots which receive the legs of the annular member.

In another preferred embodiment, the proximal end of the body includes an end wall and generally hook-shaped retainer elements disposed in confronting opposite positions proximate to the end wall. This embodiment also includes two pair of spaced ribs on opposed sides of the body which receive the syringe flange and the locking portion of the annular member. Each of the spaced ribs has an inwardly facing proximal hook-shaped end portion which receives and retains the syringe flange and an outwardly facing proximal hook-shaped end portion which receives the locking portion of the annular member. In this disclosed embodiment, the opposed sides of the proximal open end of the body also includes opposed abutment surfaces defined on posts extending from a surface of a finger grip provided at the proximal end of the body. In this embodiment, the syringe flange is substantially exposed permitting visual inspection of the securement of the syringe in the body.

Other advantages and meritorious features of the shield system of the present invention will be more fully understood from the following detailed description of the preferred embodiments, the appended claims and the drawings. As will be understood, the terms proximally and distally are used herein for descriptive purposes only and the term proximally refers to the components or portions of a component closest to the hand of the user, such as a healthcare worker or patient, and the term distally refers to the component or a portion of a component furthest from the hand of the user. Further, the preferred embodiments of the shield system for syringes described below are intended to be exemplary only and do not limit the invention except as set forth in the appended claims.

BRIEF DESCRIPTION OF THE DRAWINGS

FIG. 3 is a partial side view of FIG. 1 illustrating the interlock feature of the present invention with a partial view of a syringe shown in phantom;

FIG. 4 is a top view of FIG. 3 in the direction of view arrows 4—4;

FIG. 5 is an exploded view of the shield system shown in FIG. 1 with a conventional syringe prior to receipt of the syringe in the shield system;

FIG. 10 is a perspective side view similar to FIGS. 8 and 9 following completion of the injection and beginning of release of the plunger;

FIG. 11 is a perspective side view of the syringe and shield system following release of the plunger and extension of the needle cover or shield;

FIG. 16A is a partial cross-sectional side view of the partially assembled components of FIGS. 13 to 15 in the direction of view arrows X—X, also shown in FIG. 1;

FIG. 16B is a partial cross-sectional side view of the partially assembled components of FIGS. 13 to 15 in the direction of view arrows Y—Y, also shown in FIG. 1;

FIG. 17A is a partial cross-sectional side view of the assembled components of FIGS. 13 to 15 in the direction of view arrows Z—Z, also shown in FIG. 1;

FIG. 21 is a perspective top view of an alternative embodiment of the shield system of the present invention with a syringe assembled in the shield system;

FIG. 22 is a perspective top view of the body of the alternative embodiment of the shield system shown in FIG. 21;

DETAILED DESCRIPTION OF THE PREFERRED EMBODIMENTS

Figure 1:
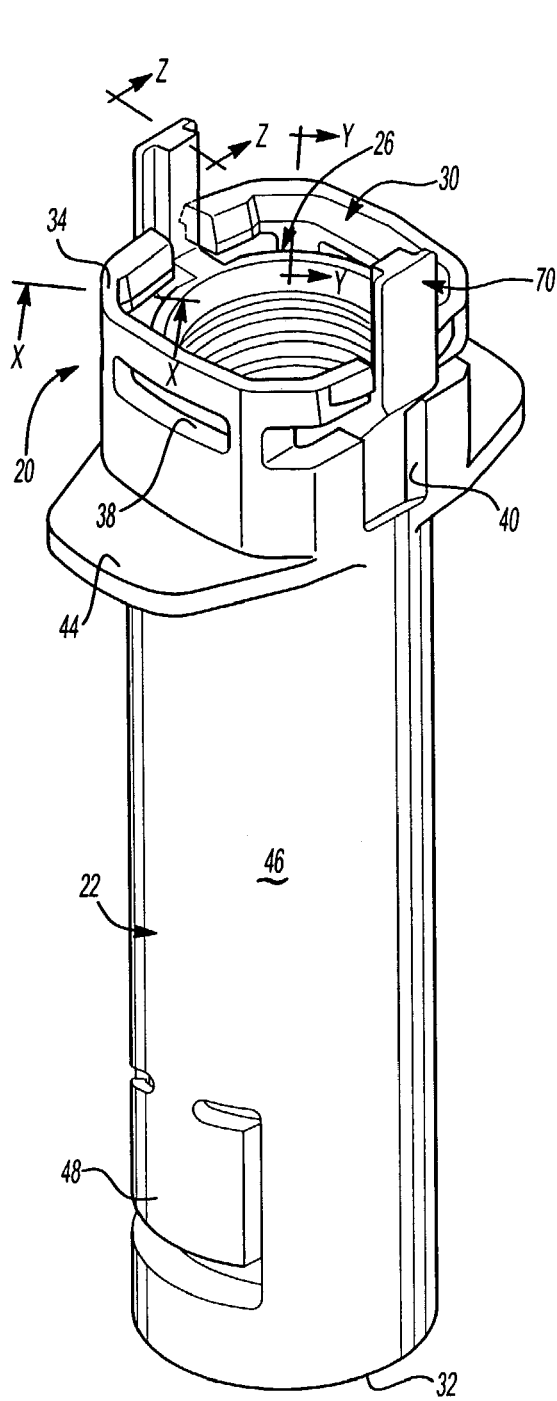
FIG. 1 is a side perspective view of one embodiment of the shield system of the present invention prior to receipt of a syringe.
Figure 2:
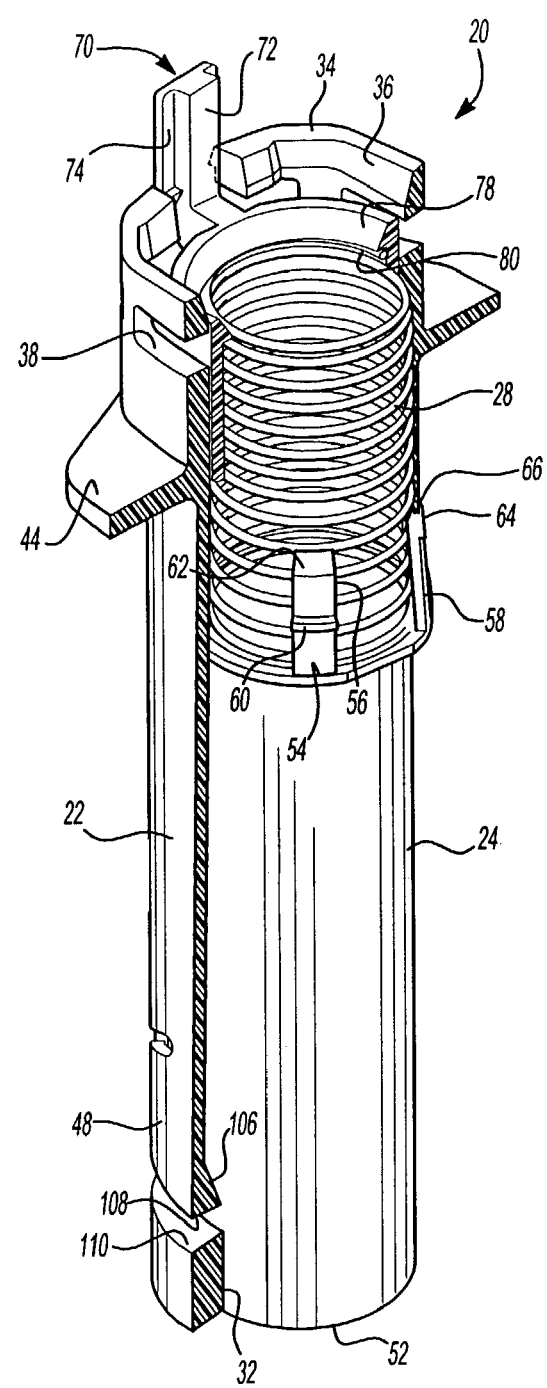
FIG. 2 is a partial cross-sectional perspective view of the shield system shown in FIG. 1.
Figure 6:
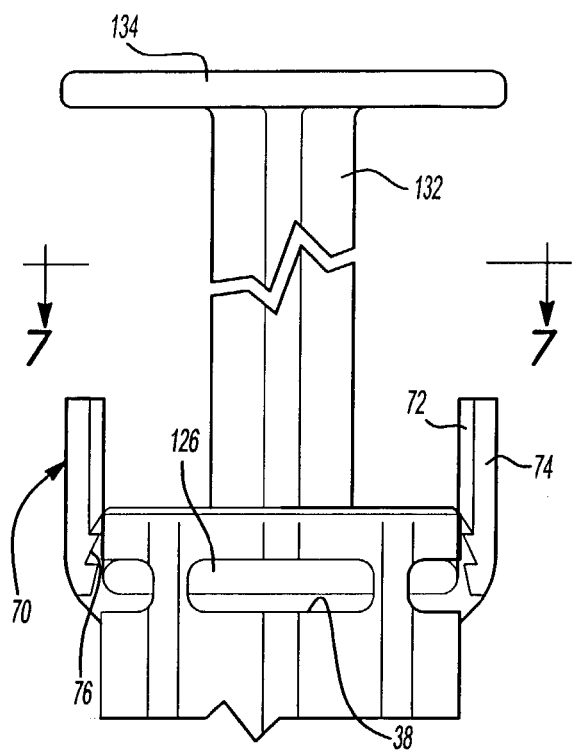
FIG. 6 is a partial side view of the proximal end of the shield system with a syringe received in the shield system.
Figure 7:
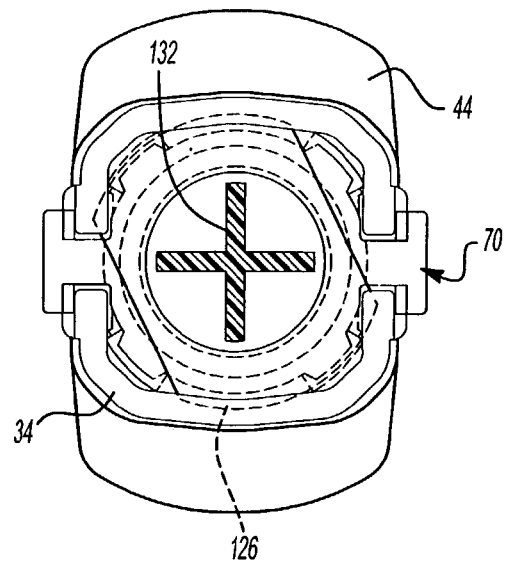
FIG. 7 is a cross-sectional end view of FIG. 6 in the direction of view arrows 7—7.
Figure 12:
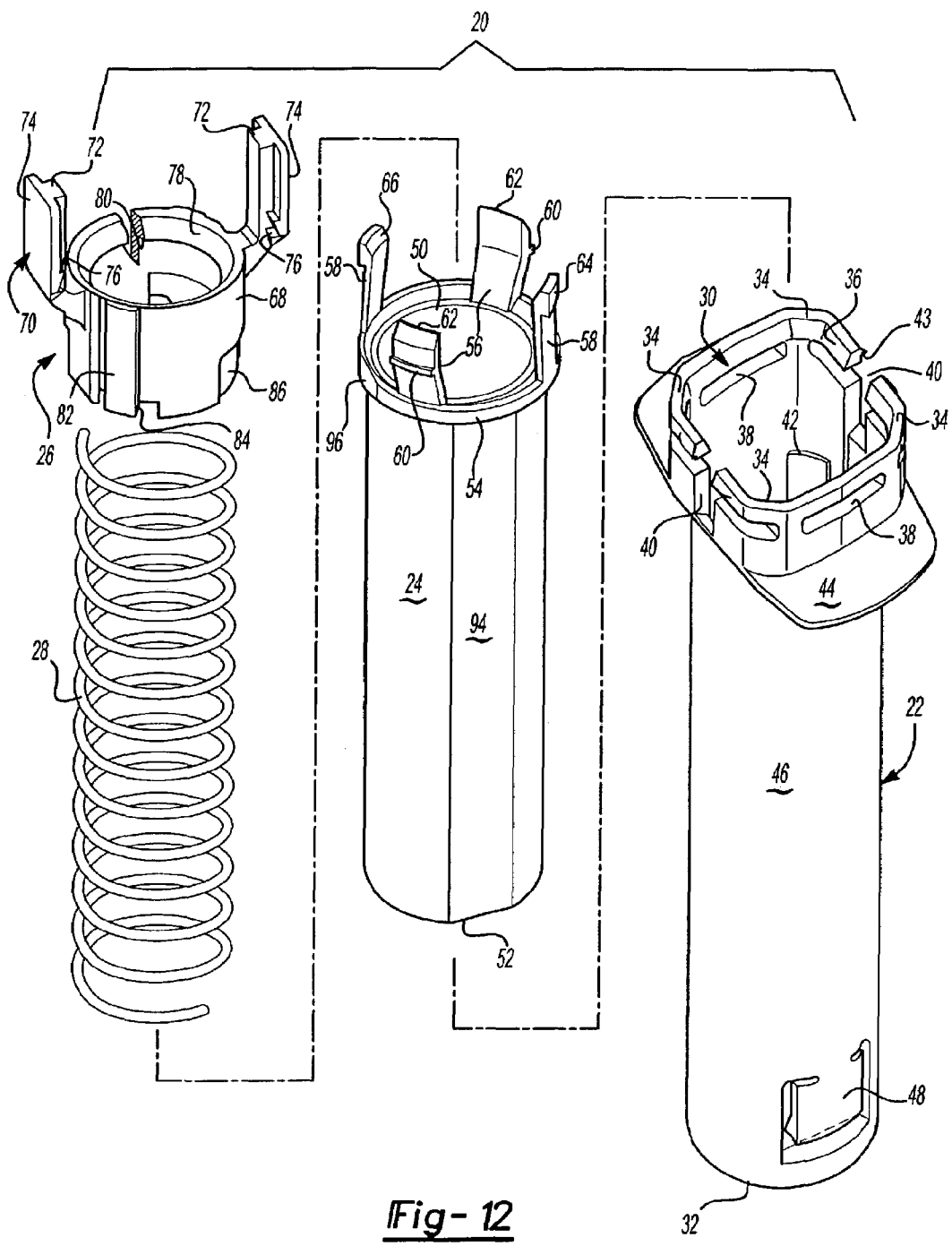
FIG. 12 is an exploded perspective side view of the components of an embodiment of the shield system of the present invention.

The shield system 20 of the present invention, a first embodiment of which is shown in FIGS. 1, 2 and 12, includes four components: a generally tubular body 22; a generally tubular needle shield 24; an annular member 26; and a spring 28. The body 22 includes an open proximal end 30 and an open distal end 32. The open proximal end 30 in the disclosed embodiment is generally rectangular or square having chamfered or truncated corners 34, inclined internal surfaces 36 at the open proximal end of the body, radial grooves 38 which receive the flange of the syringe described below, axial grooves 40 which extend through the proximal end on opposed sides which receive the legs of the annular member 26 described below, and four radial surfaces or ledges 42 at the corners 34 (see e.g., FIG. 12) which receive the radial portions of the fingers of the shield 24 as also described below. The open proximal end 30 of the body 22 may also be elliptical, oval or even cylindrical. The outer edges of the proximal end of the body 22 near the axial grooves 40 are hook-shaped having a ledge 43 which forms the interlock with the legs 70 of the annular member 26 as discussed below. The body 22 further includes opposed finger flanges 44 adjacent the open proximal end 30, a tubular barrel portion 46 which, in the disclosed embodiment, has a cylindrical outer surface but other shapes may be selected. The tubular barrel portion 46 also includes detents 48 on opposed sides which prevent retraction of the needle cover once extended as also discussed below.

Figure 13:
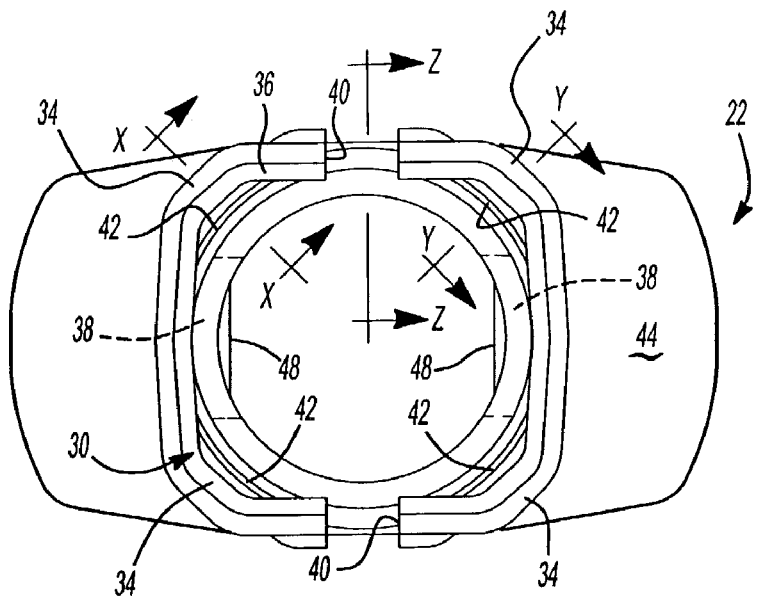
FIG. 13 is a top view of the body of the shield system.
Figure 14:
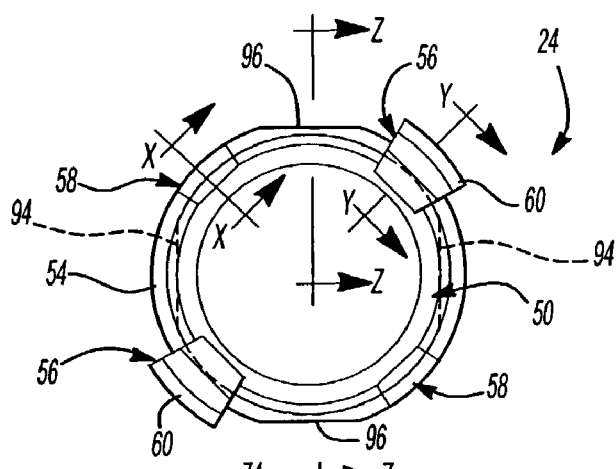
FIG. 14 is a top view of the shield of the shield system.
Figure 15:
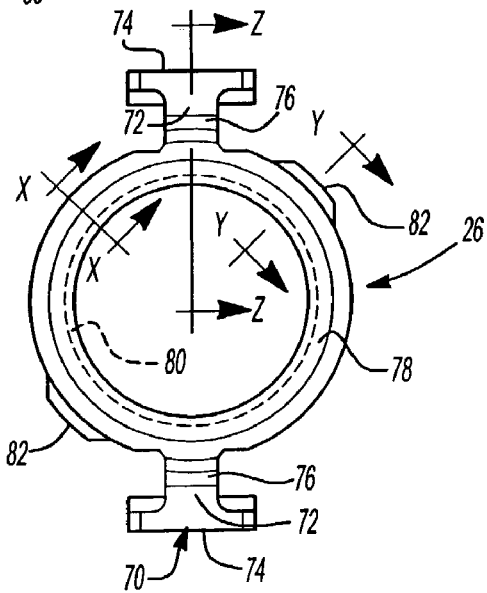
FIG. 15 is a top view of the annular or annular member.

The generally tubular needle shield 24 includes an open proximal end 50 and an open distal end 52 as best shown in FIG. 12. The shield 24 further includes an annular external rib 54 adjacent the open proximal end 50 which is received by the detents 48 (see, e.g., FIG. 13) on the distal end of the body 22 preventing retraction of the shield 24 as described below. The proximal end of the shield 24 further includes two pairs of opposed fingers including a first pair of fingers 56 and a second pair of fingers 58. As will be understood from the following description of the operation of the shield system 20 of the present invention, the terms first and second pairs of fingers are for descriptive purposes only and the shield system of the present invention may include only one finger of each of the pairs of fingers. Each of the pairs of fingers 56, 58 include a radial portion which releasably retains the needle cover 24 in a retracted position, wherein the radial portion 60 of the first pair of fingers 56 is spaced distally from the radial portion 64 of the second pair of fingers 58. The first pair of fingers 56 also include an outwardly inclined camming surface 62 at the proximal ends of the fingers and the second pair of fingers 58 include an inwardly inclined camming surface 66 at their proximal ends.

The annular member 26, also referred to as the locking member because of its function in locking the shield system prior to receipt of the syringe 120, includes an annular body portion 68 and a pair of opposed legs 70 which, in the disclosed embodiment, are generally T-shaped including an inner base portion 72 and an outer bridging portion 74. The bridging portions 74 each include a V-shaped locking portion 76 which interlocks with the ledge 43, as described below. The proximal open end of the annular member 26 includes an inclined surface 78 which tapers inwardly from the proximal open end and an abutment surface 80 at the distal termination of the inclined surface 78. The body portion 68 of the annular member 26 also includes opposed axial ribs 82 each having an outwardly inclined camming surface 84 at their distal end, best shown in FIG. 16B, and a pair of outwardly biasing surfaces 86 on opposed sides of the body portion 68 having a rounded distal end surface 88 as shown in FIG. 16A. The spring 28 is provided between the abutment surface 80 of the annular member 26 and an inner radial surface 90 of the shield 24 between the first and second pairs of fingers 56 and 58, as best shown in FIGS. 16A and 16B. The generally cylindrical outer surface of the tubular shield 24 and the radial rib 54 also include flat axially extending surfaces 94 and 96, respectively, which prevent rotation of the shield relative to the body 22 following assembly.

As set forth above, one advantage of the shield system 20 of the present invention is that it may be utilized to shield the needle cannula of an injection device such as a conventional prefilled syringe 120 shown in FIG. 5. As will be understood by those skilled in this art, a conventional prefilled syringe generally includes a tubular barrel 122 having an open proximal end 124, a radial finger flange 126 adjacent the open proximal end 124, a needle cannula 128 at the distal end of the barrel 122 and a plunger assembly comprising a stopper 130 moveable within the barrel 122, a plunger rod 132 affixed to the stopper and a thumb pad 134 at the proximal end of the plunger 132, generally unitarily formed with the rod 132. The needle cannula 128 is generally covered with a needle sheath or cap 136. The barrel 122 may be glass, plastic or metal as a routine matter of design choice. The stopper 130 is typically formed of an elastomeric material, such as rubber or synthetic rubber, but may also be formed of plastic. The plunger 132 is typically formed of plastic. However, as set forth above, the shield system 20 of the present invention may be utilized with any type of injection device and the shield system of the present invention is not limited to the types of syringes disclosed herein.

With continued reference to FIG. 12, the shield system 20 of the present invention may first be assembled by the manufacturer of the shield system prior to receipt of the syringe 120. The shield system 20 is assembled by inserting the needle shield 24 in the body 22. In the disclosed embodiment, the shield 24 is telescopically received in the open proximal end 30 of the body 22, wherein the radial portion 60 of the first pair of fingers 56 is received on the radial inner surfaces 42 of the body as best shown in FIG. 16B. Thus, the radial portion 60 of the first pair of fingers 56 limits axial movement of the tubular shield 24 in the distal direction when the shield is in the generally tubular body 46 and in the retracted position. The spring 28 is then inserted into the open proximal end 30 of the body where it is received against the radial surface 90 of the first and second pair of fingers 56 and 58 as shown in FIGS. 16A and 16B. Next, the annular member 26 is received in the open proximal end 30 of the body, wherein the proximal end of the spring 28 is received against the abutment surface 80 and the spring 28 is thus compressed between the abutment surface 80 of the annular member 26 and the opposed radial surface 90 as shown in FIGS. 16A and 16B. As shown by comparing FIGS. 16A and 16B, the first pair of fingers 56 are angled outwardly or toward the body 22, such that the radial portion 60 is received on the opposed internal radial surface 42 in the normal position. The second pair of fingers 58 are angled slightly inwardly such that the radial portion 64 of the second pair of fingers 58 will not be received on the opposed radial inner surface 42 of the body unless the fingers are biased outwardly as described below.

The annular member 26 is further compressed against the coil spring 28 until the V-shaped locking portions 76 are received beneath the abutment or hook-shaped ledge 43 of the body interlocking the shield system as described above and as shown in FIG. 17A. It should also be noted that the base portions 72 of the leg 70 are slidably received in the axial slots 40 of the body as best shown in FIGS. 1 and 2. The inwardly inclined surfaces of the V-shaped locking portion 76 resiliently bias the legs 70 outwardly to receive the transverse surface beneath the ledge 43 of the body 22. When the annular member 26 is interlocked with the body as shown in FIGS. 1 and 2, the shield system cannot be inadvertently or prematurely actuated. The shield system 20 can then be transported and processed in bulk, thereby substantially eliminating the problems associated with premature actuation of prior art shield systems during bulk handling and processing.

Figures 17B, 18A, 18B, 18C:
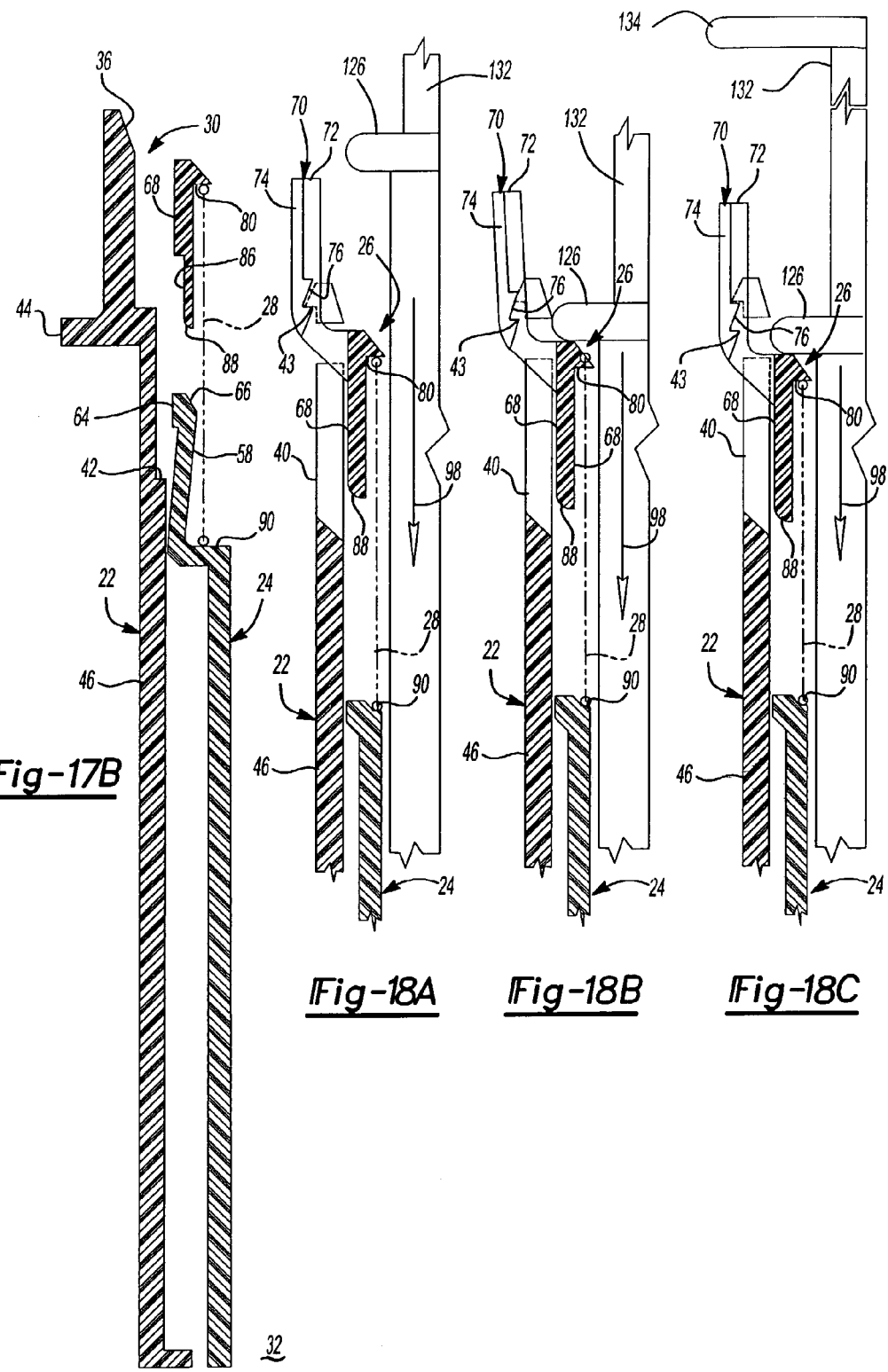
FIG. 17B is a partial cross-sectional side view of the assembled components shown in FIG. 17A in the direction of view arrows X—X.
FIGS. 18A to 18C are partial cross-sectional side views of the assembled components of FIGS. 13 to 15 in the direction of view arrows Z—Z during assembly of the syringe in the shield system.

Installation of a prefilled syringe in the open proximal end 30 of the body as shown in FIGS. 3 and 5, will now be discussed with reference to FIGS. 18A to 18C. As the barrel 122 of the syringe is received in the open proximal end 30 of the shield assembly, as shown by arrow 98, the radial flange 126 at the proximal end of the barrel 122 engages the proximal end of the annular member 26, driving the annular member 26 distally and the V-shaped surfaces 76 then resiliently bias the legs 70 outwardly as shown in FIG. 18B, thereby releasing the interlock between the body and the annular locking member 26 as shown in FIG. 18C, wherein the opposed legs 70 may now be freely moved distally in the slots 40 in the body. As shown in FIG. 18C, however, the legs cannot move proximally (i.e., toward the user) under the force of the coil spring 28 because the proximal ends of the V-shaped portions are received beneath the ledge 43 of the body. The syringe 120 is now ready for use with the radial portion 60 of the first pair of fingers 56 releasably retained on the opposed radial surface 42 of the body in a retracted position, which is referred to hereinafter as the first retracted position, as shown in FIG. 19A.

Figures 8, 9:
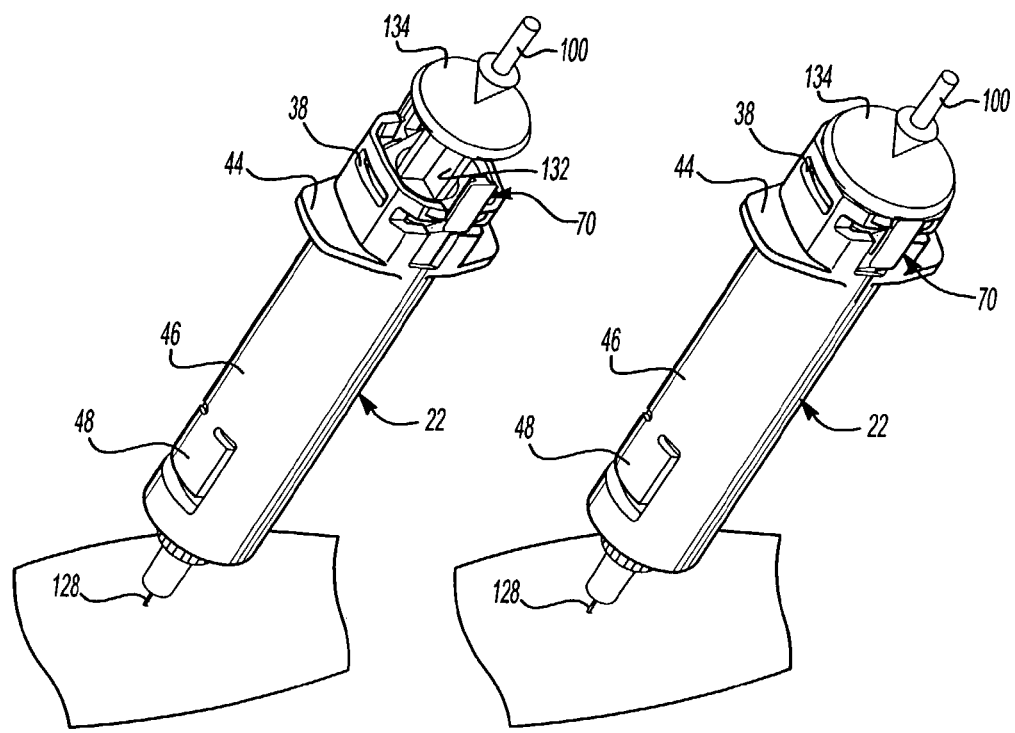
FIG. 8 is a perspective side view of the syringe and shield system assembly during use of the syringe for an injection.
FIG. 9 is a perspective side view similar to FIG. 8 upon completion of the injection.

Once the syringe 120 in the shield system 20, the syringe 120 may then be used in the same manner as a typical syringe (i.e., one without a safety shield system). After the needle cannula 128 is inserted into the patient, the end user grasps the finger flanges 44 of the body 22 and depresses the thumb pad 134, as shown by arrow 100 in FIG. 8, to make an injection. As the thumb pad 134 is depressed to make the injection, it is moved toward the legs 70 of the annular member 26 as shown in FIGS. 9 and 19B. Because the legs 70 of the annular member 26 are free to move axially and distally in the slots 40 of the body 22, continued depression of the thumb pad 134 by the user drives the thumb pad against the legs 70 and the annular member 26 is thus moved distally as shown in FIG. 19B, wherein the rounded end 88 of biasing surface 86 of the annular member 26 first engages the camming surface 66 and the biasing surface 86 then biases the second pair of legs 58 toward the radial surfaces 42 of the body 22 such that the radial portions 64 of the second pair of fingers 58 are aligned with the internal radial surfaces 42 of the body as shown in FIG. 19B. Continued depression of the thumb pad 134 drives the annular member 26 distally, driving the outwardly inclined camming surfaces 84 against the opposed camming surfaces 62 of the first pair of fingers 56, resiliently biasing the first pair of fingers 56 away from the body 22 or radially inwardly as shown in FIG. 19C, wherein the radial portions 60 are released from the opposed radial surfaces 42 of the body.

Figure 19A:
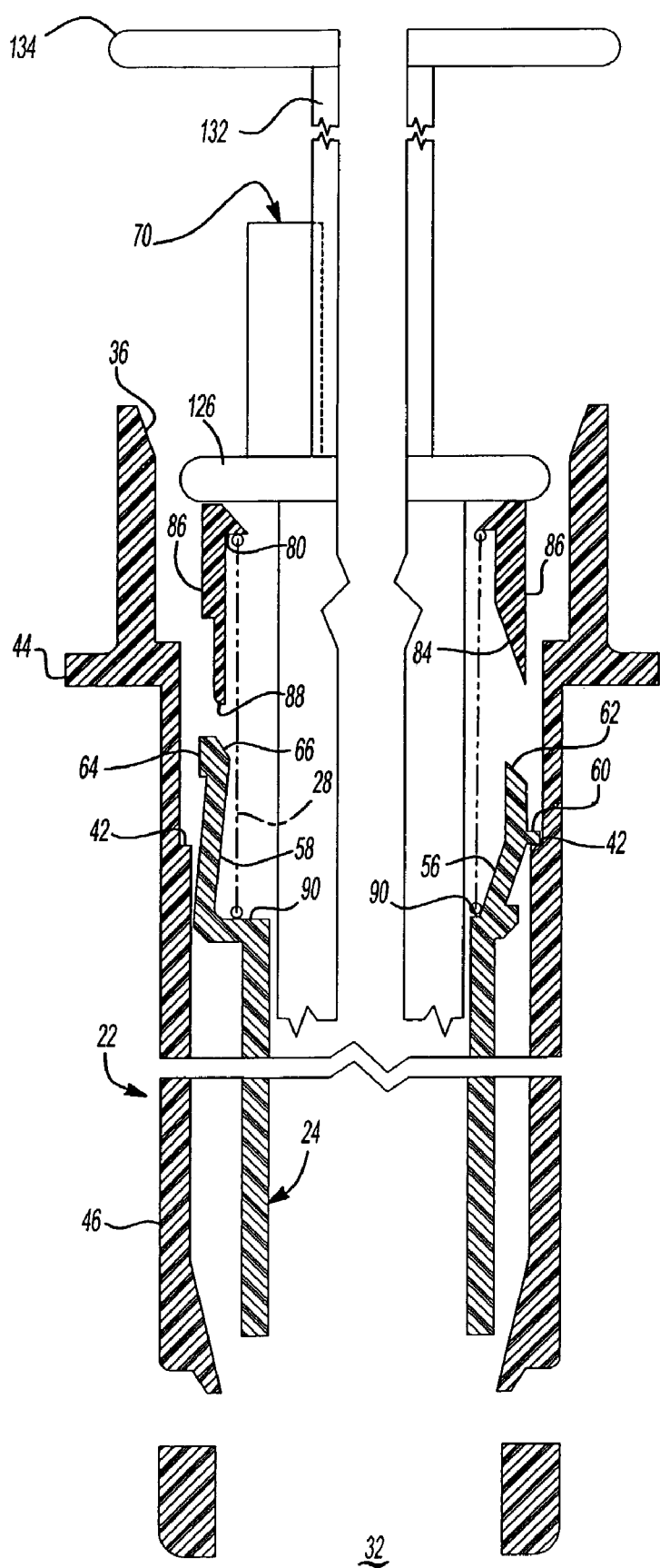
FIGS. 19A to 19E are partial cross-sectional side views of the syringe and shield assembly during injection and actuation of the shield, wherein the left-hand portion is a partial cross-section through view arrows X—X and the right-hand portion is a partial cross-section through view arrows Y—Y.
Figure 19B:
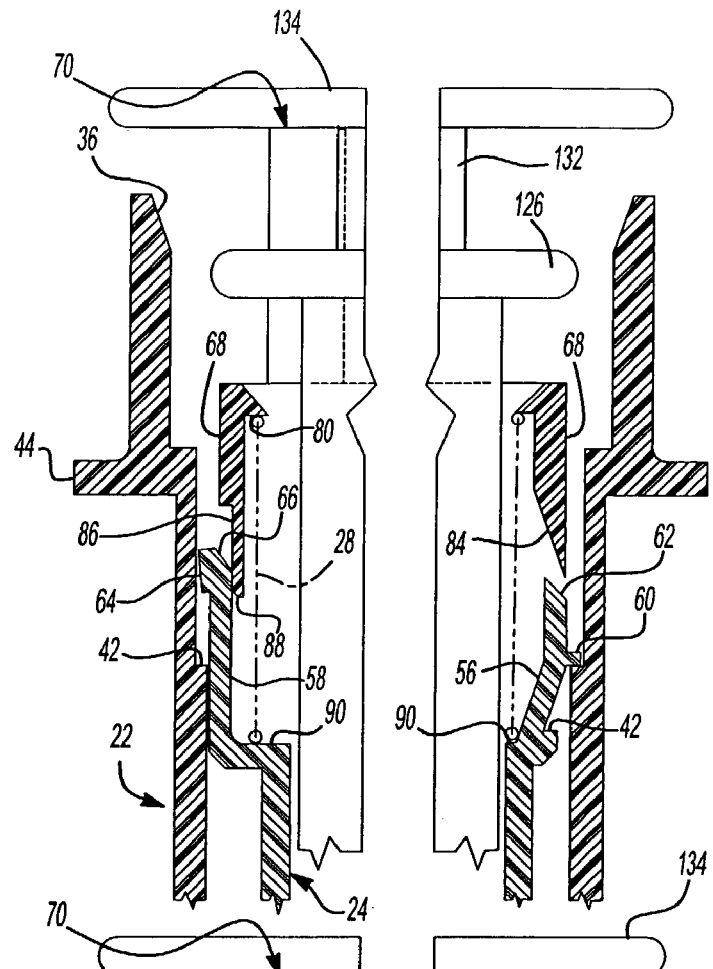
Figure 19C:
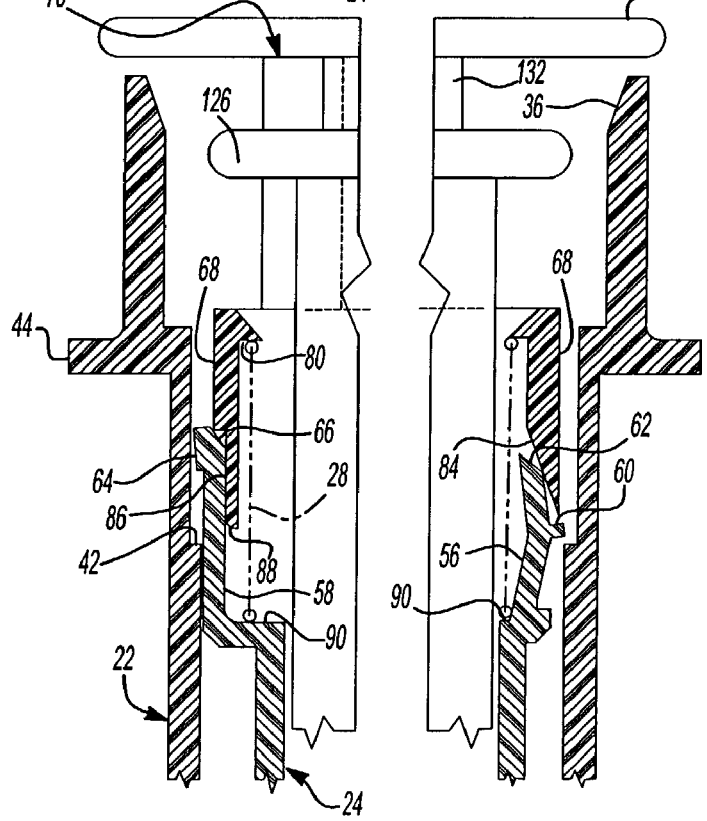
Figure 19D:
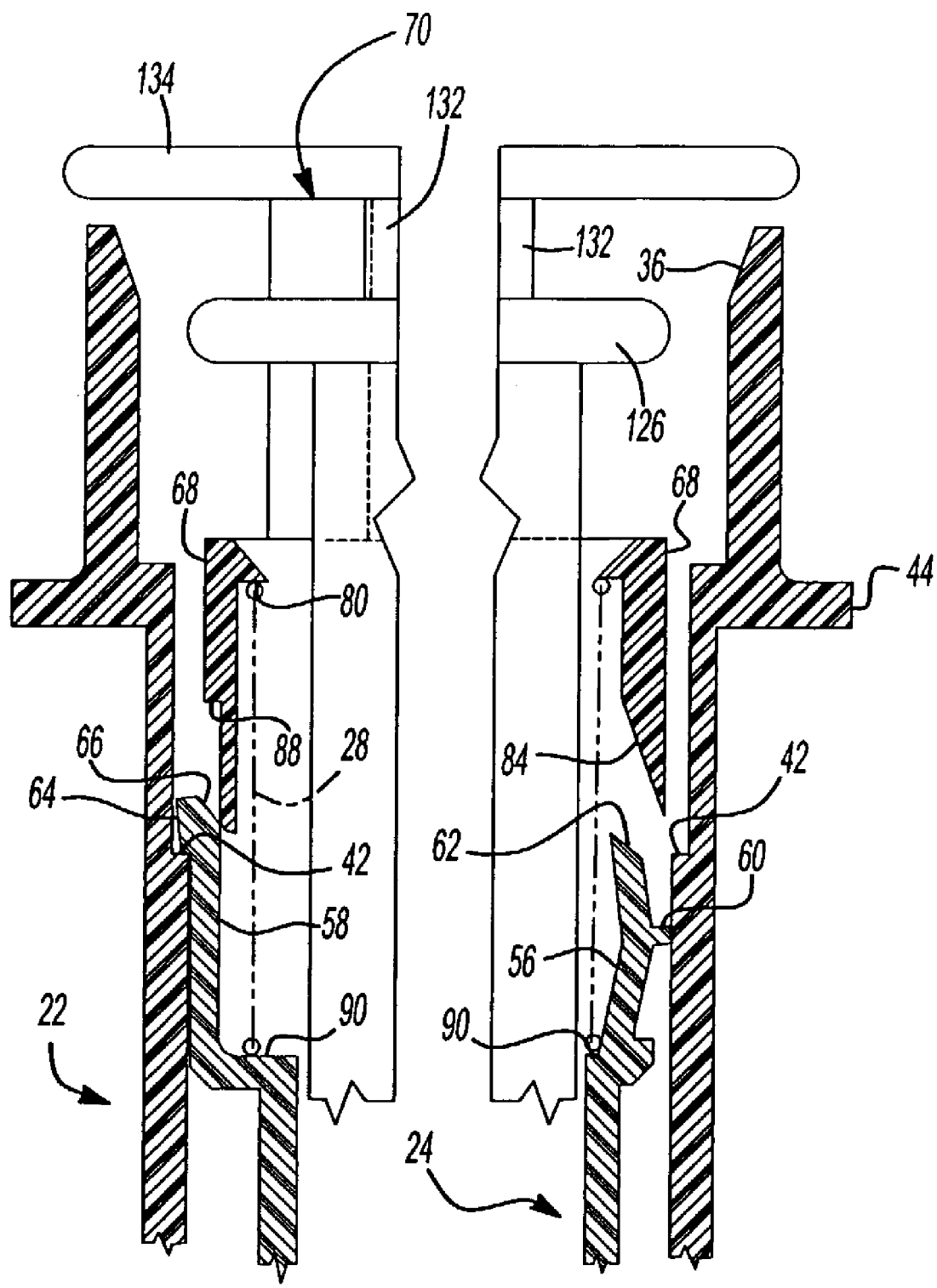

The shield 24 then moves distally relative to syringe 120 and body 22 under the force of the spring 28 as shown in FIG. 19D to a second retracted position, wherein the radial portions 64 of the second pair of fingers 58 are received on the opposed radial surfaces 42 of the body and maintained in the second retracted position by the biasing surfaces 86 of the annular member 26, and the radial portion 60 of the first pair of fingers 56 are spaced distally from the opposed radial surfaces 42 of the body as shown in FIG. 19D. As will then be understood from FIG. 19D, the shield 24 is thus releasably retained in the second retracted position as long as the thumb pad 134 of the plunger is maintained by the user. Thus, release of the shield 24 so as to contact the patient's skin can be prevented by the user, who controls release of the shield 24 by release of the thumb pad 134.

Figure 19E:
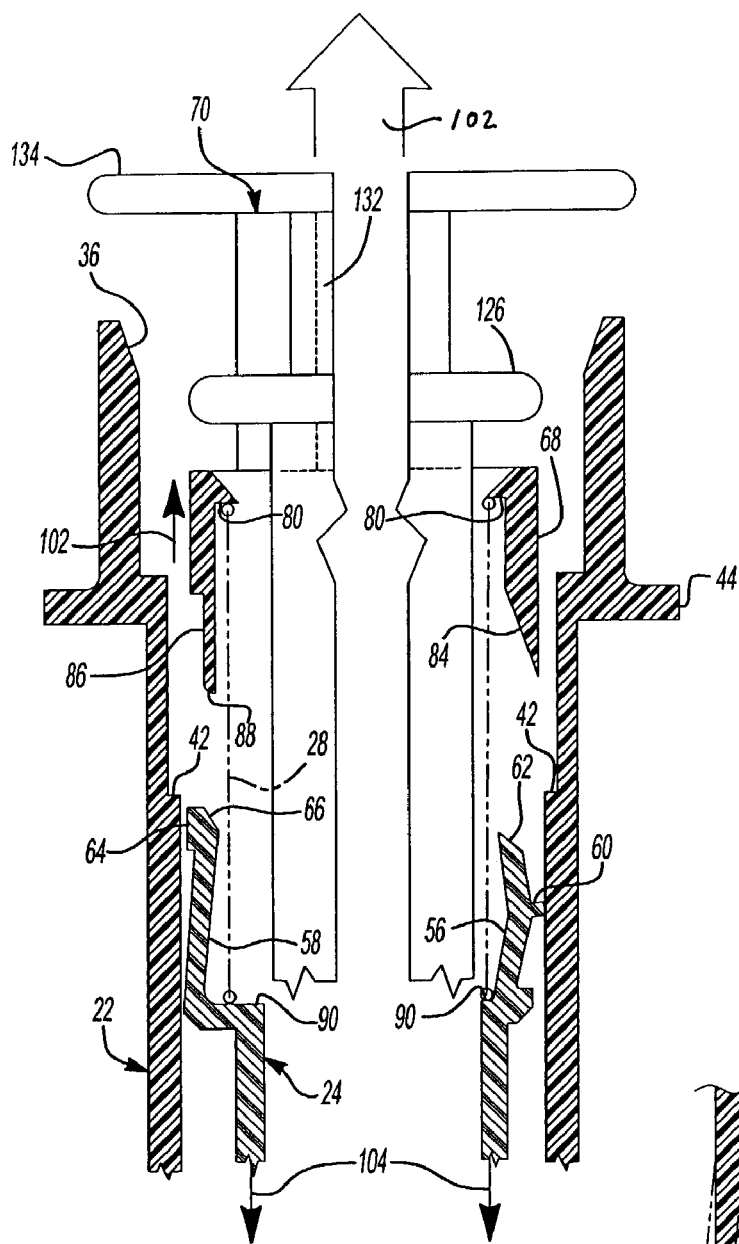
Figure 20:
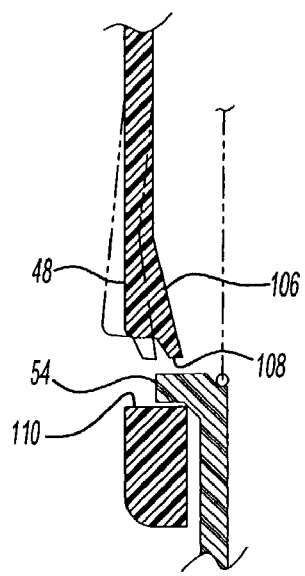
FIG. 20 is a partial cross-sectional side view of the distal end portion of the body and the proximate end portion of the shield illustrating locking of the shield in the extended position.

When the thumb pad 134 is released by the user, the spring 28 drives the annular member 26 proximally as shown by arrow 102 in FIG. 19E, releasing the second pair of fingers 58 and resulting in radial inward movement of the second pair of fingers 58, and release of the radial portions 64 of the second pair of fingers from the opposed radial surfaces 42 of the body. The shield 24 is then driven distally by the spring 28 as shown by arrows 104 in FIG. 19E and the shield 24 is thus extended from the second retracted position shown in FIG. 19D to the extended position, as shown in FIG. 11 where the shield 24 fully encloses the needle cannula 128 of the syringe. The shield 24 is then locked in the extended position by the detents 48 adjacent the distal end of the body 22 as shown in FIG. 20, wherein, as the shield 24 is caused to move (by the spring 28) from the second retracted position to the extended position, the radial rib 54 of the shield 24 engages the inwardly inclined surface 106, resiliently biasing the detents 48 radially outwardly as shown in phantom in FIG. 20 to receive the radial rib 54 between the opposed abutment surfaces 108 and 110 of the detent. Thus, the shield 24 cannot be retracted from the extended position and the needle cannula 128 is completely enclosed by the shield 24 as shown in FIG. 11. The syringe 120 and shield system 200f the present invention may thus be disposed of without potential needle sticks to the persons handling the syringe following injection.

As will now be understood, the user can thus select the timing of the actuation of the shield of the present invention. That is, the user can remove the needle cannula 128 from the patient prior to releasing the thumb pad 134, such that the shield 24 does not contact the skin of the patient, which is generally considered undesirable. Alternatively, the user can release the thumb pad following injection while the needle cannula 128 remains in the patient, thereby releasing the shield 24.

The embodiment of the shield system 220 illustrated in FIGS. 21 to 25 may be substantially identical to the shield system 20 illustrated in FIGS. 1 to 20 except for the means of retaining the syringe 120 in the body 222. Except for the body 222, the components of the shield system 220 depicted in FIGS. 21 to 25 may be identical to the shield system 20 described above and shown in FIGS. 1 to 20, including the shield 24, the annular member 26 and the spring 28. Further, the operation of the shield system 220 may be substantially the same as described above. Thus, only the modified generally tubular body 222 need be described herein in detail for a complete understanding of the shield system 220 shown in FIGS. 21 to 25.

Figure 23:
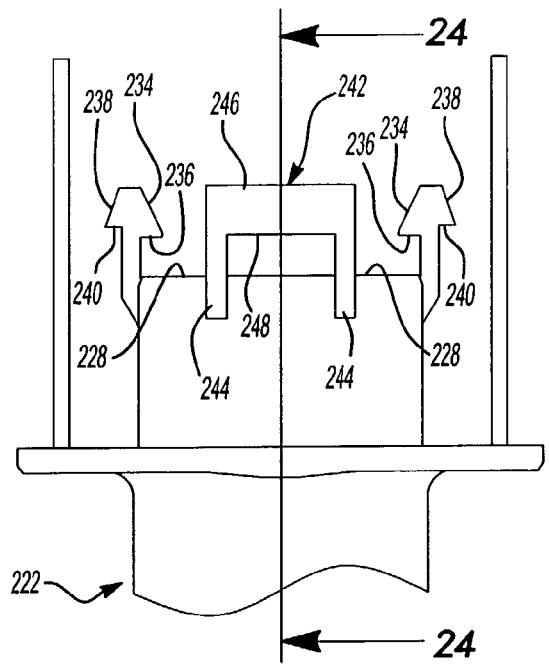
FIG. 23 is a partial side view of the body of the shield system shown in FIG. 22.
Figure 24:
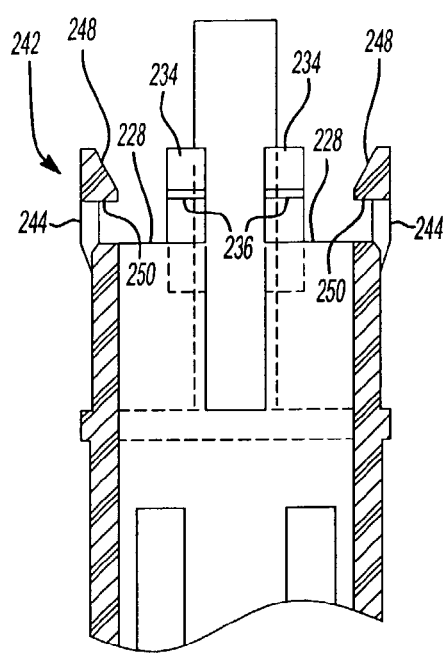
FIG. 24 is a cross-sectional side view of FIG. 23 in the direction of view arrows 24—24.

Referring first to FIGS. 22 to 24, which illustrate the alternative embodiment of the body 222, the generally tubular body 222 includes an open proximal end 224, which receives the barrel 122 of the syringe 120, and an open distal end 226 as described above in regard to FIG. 5. The open proximal end 224 is generally rectangular or square in shape and is generally delineated by an end wall 228 having chamfered or truncated corners 230. However, the shape of the proximal end of the body 222 may be any convenient shape, as a routine matter of design choice. The proximal end of the body 222 includes a plurality of generally hook-shaped retainer elements 242 disposed circumferentially about and which project from, the proximal end 224 of the end wall 228. The retainer elements 242 retain the syringe 120 in the body 222.

Figure 25:
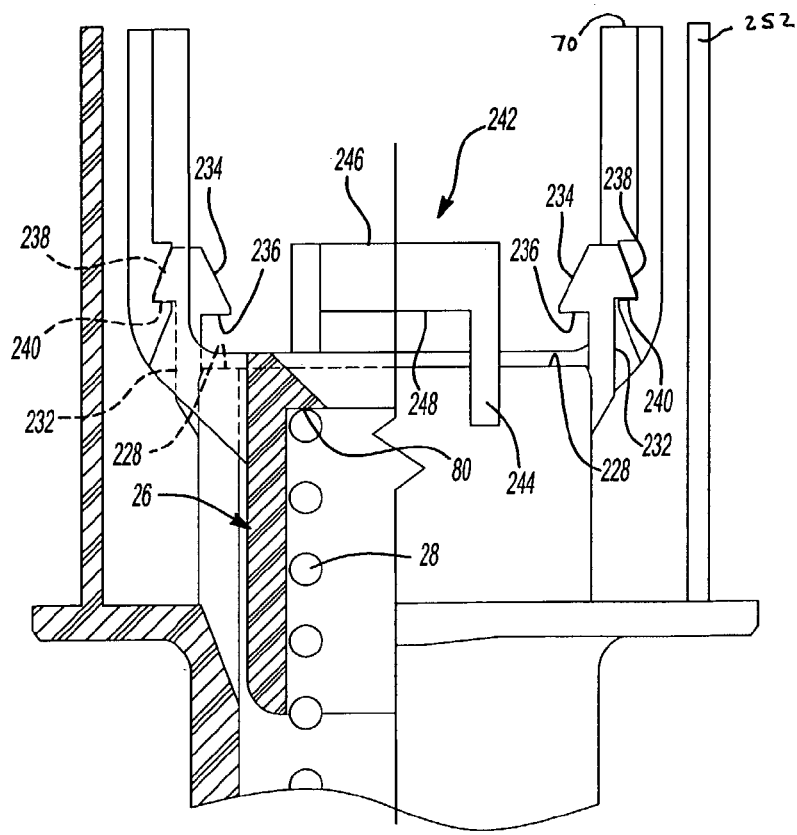
FIG. 25 is a partial cross-sectional side view of the shield system illustrated in FIG. 21 prior to receipt of the syringe.

The retainer elements 242 include two pair of opposed spaced integral ribs 232 (i.e., from ribs in a preferred embodiment) which project axially with the body 222 and from the end wall 228 on opposed sides of the open proximal end 224. Each rib 232 has an inclined inner surface 234 terminating in an undercut 236, and an inclined outer surface 238 terminating in an undercut 240. As described below, the ribs 232 receive the axially projecting legs 70 of the annular member 26 therebetween as shown in FIGS. 21 and 25. The retainer elements 242 also include posts 244 which project axially with the body 222 and from the open proximal end 224 and include a bridging portion 246. Each such retainer element 242 has an inclined camming surface 248 and an undercut 250. As shown in FIGS. 23 and 24, the undercuts 236 and 248 are aligned and shaped to form confrontingly opposite abutment surfaces with the opposed end wall 228. Thus, as described above, the syringe 120 is received in the open proximal end 224 of the body 222 as shown in FIG. 5, wherein the flange 126 of the barrel 120 of the syringe 120 is received against the inwardly inclined surfaces 234 and 248. As the syringe 120 is pushed into the body 222, interaction between the flange 126 and surfaces 234, 248 causes resilient biasing of the retainer elements 242 outward so as to permit the syringe flange 126 to pass and be retained by the retainer elements 242. The retainer elements 242 receive the flange 126 of the syringe 120 and hold it between the undercuts 236 and 250 of the retainer elements 242 and the opposed end wall 228 of the body, retaining the syringe 120 in the body 222. One advantage of this means of retaining the syringe in the body is that the flange 126 of the syringe is exposed, permitting inspection of the retainer elements following assembly to confirm that the syringe is securely retained in the body following assembly.

As described above with regard to the assembly of the shield system 20 depicted in FIGS. 1 to 20, the needle cover or shield 24 (not shown in FIGS. 21 to 25) but described above, is first received in the body, then the spring 28 and the annular member 26. The legs 70 of the annular member 26 are received between the ribs 232 and the V-shaped locking portions 76 interlock with the inclined outer surfaces 238 and the undercut 240 as shown in FIG. 25. Thus, the assembly of the shield system 220 is substantially identical to the assembly of the shield system 20 described above, wherein the locking member 26 forms an interlock with the proximal end of the body prior to receipt of the syringe 120 so as to prevent premature or inadvertent actuation of the shield system 20.

This embodiment of the shield system 220 of the present invention includes a further optional security feature for reducing the likelihood of premature or inadvertent actuation of the shield system. Protective walls 252 are provided proximate the ribs 232 which receive the projecting legs 70 of the annular member 26 as shown in FIGS. 21 and 25. The protective walls 252 preferably extend beyond the end of the projecting legs 70, thereby reducing the likelihood of inadvertent contact with the legs 70 during shipping and handling and by the user. The protective walls 252 are planar and integrally formed with the finger grip 254 and extend generally perpendicularly therefrom. However, the walls can be arcuate, for example, to partially surround the legs 70 or any other shape as long as it provides the desired functionality as described herein.

As described above, the shield system 220 is actuated by engagement of the thumb pad 134 and projecting legs 70. That engagement causes the annular member 26 to be displaced distally. Then upon release of the thumb pad 134, the shield 24 is released and the spring 28 then drives the shield 24 to the extended position shown in FIG. 11. The protective walls 252 are spaced from the ribs 232 sufficient to accommodate the receipt of the thumb pad 134 between the walls 252, while still reducing the likelihood of inadvertent engagement of the legs 70.

As described above, the shield is preferably locked in the extended position following actuation and the disclosed embodiment of the body 222 includes detents 256 which lock the shield 24 in the extended position as described above. As set forth above, except for body 222, the remaining components of the shield system 220 may otherwise be identical to the components of the shield system 20, depicted in FIGS. 1 to 20, and described in detail herein.

Based upon the above description of the preferred embodiments of the shield system 20, 220 of the present invention, the assembly of the shield system and method of operation, the method of assembling a shield system 20 on a syringe 120 comprises assembling the shield system 20 including the generally tubular body 22, the generally tubular needle cover or shield 24, the spring 28, and the annular member 26, wherein the shield 24 is in a retracted position and the annular member 26 is interlocked with the body 22, preventing inadvertent or premature release of the shield from the retracted position to the extended position prior to receipt of the syringe in the shield system 20. The method then includes inserting a syringe 120 in the shield system 20 through the open proximal end 30 of the body 22, thereby releasing the locking member 26 from the body and permitting user-controlled actuation of the shield as described above.

The components of the shield systems 20 of the present invention may be formed of various materials. For example, the body 22, needle shield 24 and the annular member 26 may be formed of plastic including clear plastic for visualization of the content of the syringe 120. The body 22 and needle shield 24 are preferably formed of a resilient or semi-rigid plastic for operation of the interlock and release of the shield as described above. As will be understood by those skilled in this art and from the disclosure provided herein, various modifications may be made to the shield systems 20 and 220 of the present invention without departing from the scope or spirit of the invention. For example, features of the shield system of the present invention can be incorporated in a shield system wherein the shield is telescopically received around the exterior surface of the body, particularly including the interlock feature. Further, the annular member 26 may include only one leg 70 or a plurality of legs greater than two. Although the annular member 26 is preferably ring shaped as disclosed, other shapes may also be utilized. Further, as described above, the fingers 56 and 58 of the needle shield 24 are preferably opposed pairs of fingers as disclosed providing balanced support of the shield, the shield system of the present invention may include only two fingers or a plurality of fingers greater than two. Finally, the internal radial support surfaces 42 in the body, which releasably support the needle cover in the body, may be spaced axially for each of the pairs of fingers, wherein the radial portions would be adjusted axially accordingly. Having described the preferred embodiments of the passive safety shield system for syringes of the present invention and method of assembly and operation, the invention is now claimed as follows.

The invention claimed is:

1. A shield system for a syringe, the syringe having a tubular barrel having a distal end with a needle cannula extending therefrom, and an open proximal end having a flange defined thereabout, the syringe including a stopper in the barrel, a plunger coupled with the stopper and extending from the open proximal end and having a thumb pad at a proximal end of the plunger, said shield system comprising:

a generally tubular body having an end wall and an open proximal end having means for receiving the syringe;

a generally tubular shield telescopically supported by said body and movable relative thereto from a first retracted position in which the needle cannula is exposed, to a second retracted position which is axially spaced from said first retracted position and in which the needle cannula is exposed, to an extended position in which the needle cannula is enclosed by said shield;

a spring supported in said body and biasing said shield toward said second retracted position and said extended position;

a locking member supported by said body for axial movement with respect thereto, said locking member being disposed in a locking position prior to retention of the syringe in said body, distal axial movement of said locking member releasing said tubular shield from said first retracted position and securing said shield in said second retracted position, proximal axial movement of said locking member releasing said tubular shield from said second retracted position and enabling said tubular shield to move to said extended position;

first retainer elements defined about said open proximal end of said body for retaining said locking member in said locking position to prevent inadvertent release of said shield from said first retracted position prior to retention of the syringe in said body; and second retainer elements defined about said open proximal end of said body for retaining the syringe in said body.

2. The shield system for a syringe as recited by claim 1, wherein said shield includes a first pair of fingers having a radial portion and extending axially therewith from a proximal end thereof, and wherein said body includes a radial surface, said radial portion of said first pair of fingers releasably interacting with said radial surface of said body to releasably support said shield in said first retracted position.

3. The shield system for a syringe as recited by claim 2, wherein said shield includes a second pair of fingers having a radial portion proximally axially displaced from said radial portion of said first pair of fingers, said radial portion of said second pair of fingers releasably interacting with said radial surface of said body to releasably support said shield in said second retracted position.

4. The shield system for a syringe as recited by claim 3, wherein each of said first pair of fingers is biased toward said radial surface of said body, and each of said second pair of fingers is biased away from said body, said locking member being moveable axially with said body by the plunger, said locking member including a first camming surface for engagement with each of said first pair of fingers to bias each of said fingers away from said body thereby releasing said shield from said first retracted position, said locking member further including a second camming surface for engagement with each of said second pair of fingers to bias each of said fingers toward said body thereby releasably securing said shield in said second retracted position.

5. The shield system for a syringe as recited by claim 4, wherein said spring is biased between said locking member and said shield such that release of the plunger assembly causes said spring to move said locking member proximally thereby releasing each of said second pair of fingers, said spring then causing said shield to move from said second retracted position to said extended position.

6. The shield system for a syringe as recited by claim 1, wherein when said locking member maintains said shield in said second retracted position until release by a user of the plunger.

7. The shield system for a syringe as recited by claim 1, wherein said locking member is annular having a proximally projecting leg portion releasably mechanically interlocked with said first retainer elements prior to retention of the syringe in said body.

8. The shield system for a syringe as recited by claim 1, wherein said locking member is received in said open proximal end of said body and said spring is positioned between said locking member and said shield.

9. The shield for a syringe as recited by claim 1, wherein said first retainer elements comprise two pair of opposed spaced integral ribs projecting axially with said body and from an end wall thereof and on opposed sides of said open proximal end of said body, each rib having an inclined inner surface terminating in a first undercut and an inclined outer surface terminating in a second undercut.

10. The shield for a syringe as recited by claim 1, wherein said second retainer elements comprise posts projecting axially with and from said open proximal end of said body, said second retainer elements including a bridging portion and an inclined camming surface and an undercut, said undercuts being aligned and shaped to form confrontingly opposite abutment surfaces with said end wall of said body.

11. A shield system for a syringe as recited by claim 1, further comprising a protective wall extending proximally from said body adjacent said locking member and being sized and shaped to limit access to said locking member so as to prevent inadvertent actuation of said shield.

* * * * *